(12) United States Patent
Sigalas et al.

(10) Patent No.: US 7,466,410 B2
(45) Date of Patent: Dec. 16, 2008

(54) PHOTONIC-BASED SENSORS AND METHODS FOR DETECTING ANALYTES

(75) Inventors: Mihail Sigalas, Santa Clara, CA (US);
David Fattal, Mountain View, CA (US);
Jason Blackstock, Cambridge, MA (US); Raymond G. Beausoleil, Redmond, WA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 121 days.

(21) Appl. No.: 11/698,320

(22) Filed: Jan. 26, 2007

(65) Prior Publication Data

US 2008/0180672 A1 Jul. 31, 2008

(51) Int. Cl.
*G01J 3/18* (2006.01)
*G01J 3/42* (2006.01)

(52) U.S. Cl. .......................................... 356/328; 385/12

(58) Field of Classification Search ................. 356/328; 385/12
See application file for complete search history.

(56) References Cited

U.S. PATENT DOCUMENTS

2006/0291766 A1* 12/2006 Schulz et al. ................. 385/12

* cited by examiner

*Primary Examiner*—F. L Evans

(57) ABSTRACT

Various embodiments of the present invention are directed to analyte detection methods and to photonic-based sensors that employ photonic crystal gratings to detect analytes. In one embodiment of the present invention, a photonic-based sensor includes a source, a photonic crystal, and a photodetector. The source is configured to output electromagnetic radiation. The photonic crystal includes a photonic crystal grating positioned to receive the electromagnetic radiation. The electromagnetic radiation interacts with the photonic crystal grating and an analyte situated on or in the photonic crystal grating to produce a transmission spectrum that characterizes the analyte. The photodetector is positioned to detect the transmission spectrum.

20 Claims, 11 Drawing Sheets

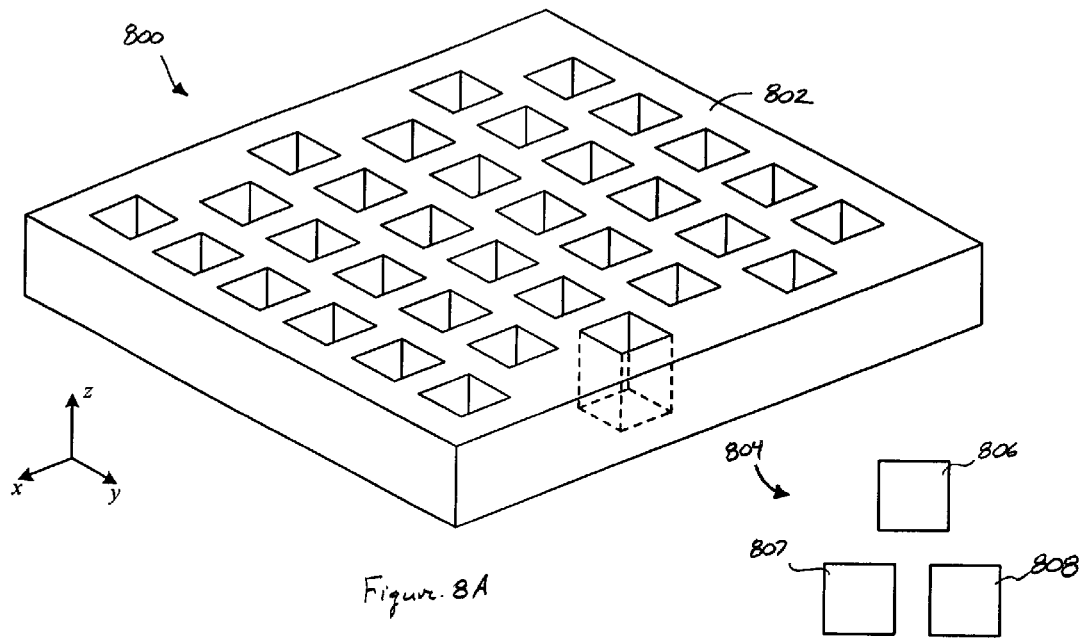
Figure 8A
Figure 8B
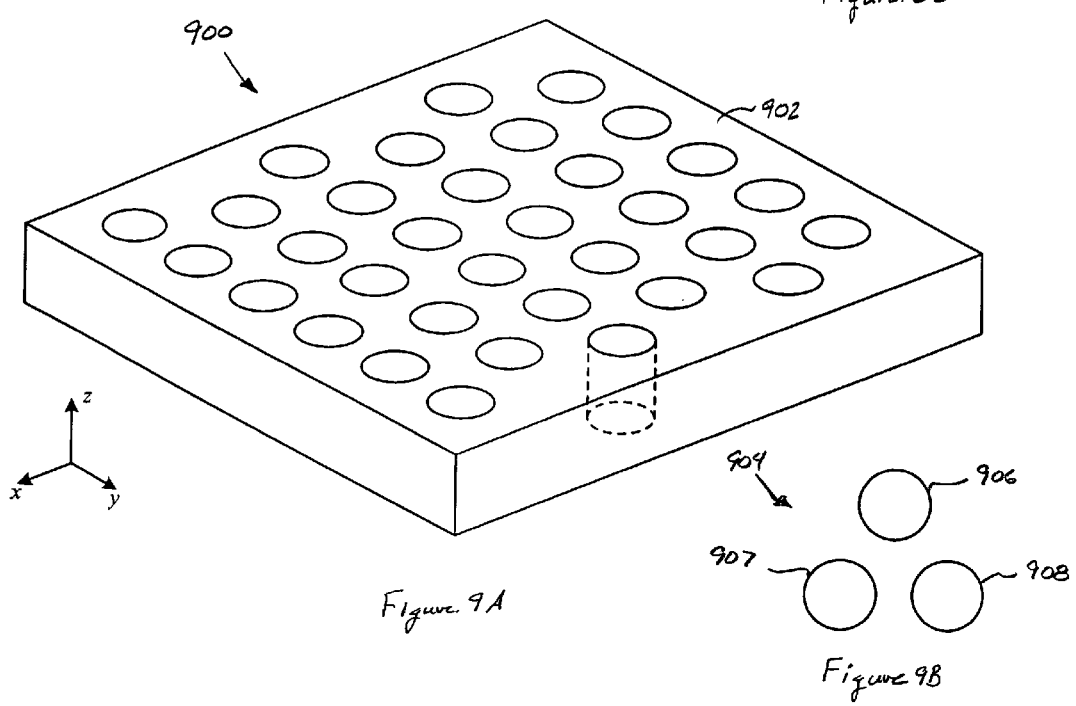
Figure 9A
Figure 9B

PHOTONIC-BASED SENSORS AND METHODS FOR DETECTING ANALYTES

TECHNICAL FIELD

Systems and methods of the present invention relate to chemical sensors, and, in particular, to methods for detecting analytes and to photonic-based sensors that employ dielectric or semiconductor photonic crystal gratings to detect analytes.

BACKGROUND

Analyte detection technology is currently employed in a wide range of disciplines ranging from electrochemical analysis, through measurements to detect the presence and amount of biological compounds, to pollution monitoring and industrial control. For example, chemical sensors have been developed to determine carbon dioxide levels in underground parking structures and in industrial manufacturing plants and to detect certain toxic chemicals in homes and in coal mines. Federal, state, and local governments have become increasingly aware of the dangers of airborne pollutants and have begun to regularly monitor the levels of pollutants using chemical sensors. In addition, the threat of terrorist attacks employing toxic chemical weapons, such as sarin gas, has created public concern and a demand for chemical sensors that can detect particular chemical weapons so that government authorities can respond accordingly. In the medical fields, a class of chemical sensors called "biosensors" have been developed to detect quantities of certain biological compounds.

Although advancements in engineering and scientific disciplines have made it possible to fabricate chemical sensors to detect a variety of different analytes, a typical chemical sensor is often limited to detection of a single analyte or a small number of different kinds of analytes. In addition, a number of steps may be needed to prepare an analyte for detection. For example, certain optical chemical sensors employ a fluorescent material immobilized on an optical-fiber core. An analyte is detected by observing a color change that results from the fluorescent material reacting with the analyte. However, in order to detect a different analyte, the fluorescent material needs to be changed to one that fluoresces when reacted with the different analyte. Certain types of biosensors may employ active biological or biologically derived components which form chemical bonds with an analyte and hold the analyte in position for detection by a chemical sensor. An indirect approach is to use an enzyme that catalyzes a chemical reaction when an analyte is present to produce a product that can be detected by a chemical sensor. The presence of the product confirms the existence of the analyte.

In recent years, photonic-based sensors have been developed to detect and quantify the amount of an analyte. Photonic-based sensors typically employ gratings that support the analyte during irradiation. Examples of photonic-based sensors employing metallic gratings to characterize and determine quantities of biological compounds are described in the following articles: M. U. Pralle, et al., "Photonic crystal enhanced narrow-band infrared emitters," Appl. Phys. Lett. 81, 4685 (2002), and A. G. Brolo, et al., "Surface plasmon sensor based on the enhanced light transmission through arrays of nanoholes in gold films," Langmuir 20, 4813 (2004). Examples of photonic-based sensors employing dielectric gratings are described in the following articles: B. Cunningham et al., "A plastic colimetric resonant optical biosensor for multiparallel detection of label-free biochemical interactions," Sensors and Actuators B 85, 219 (2002), and N. Ganesh et al., "Near ultraviolet-wavelength photonic crystal biosensor with enhanced surface to bulk sensitivity ratio," Appl. Phys. Lett. 89, 023901 (2006). However, photonic-based sensors typically exhibit significant energy losses and the resonance frequency of the gratings can be low. In addition, it may be difficult to determine the presence of certain biological analytes because many biological analytes do not adhere to the gratings. Physicists, engineers, and those employing chemical sensors to detect analytes have recognized a need for photonic-based sensors that provide improved sensitivity and can be used to detect a large number of different analytes.

SUMMARY

Various embodiments of the present invention are directed to analyte detection methods and to photonic-based sensors that employ photonic crystal gratings to detect analytes. In one embodiment of the present invention, a photonic-based sensor includes a source, a photonic crystal, and a detector. The source is configured to output electromagnetic radiation. The photonic crystal includes a photonic crystal grating positioned to receive the electromagnetic radiation. The electromagnetic radiation interacts with the photonic crystal grating and an analyte situated on or in the photonic crystal grating to produce a transmission spectrum that characterizes the analyte. The photodetector is positioned to detect the transmission spectrum.

BRIEF DESCRIPTION OF THE DRAWINGS

FIG. 8A illustrates an isometric view of a third two-dimensional photonic crystal that represents an embodiment of the present invention.

FIG. 8B illustrates a unit cell of the photonic crystal shown in FIG. 8A that represents an embodiment of the present invention.

FIG. 9A illustrates an isometric view of a fourth two-dimensional photonic crystal that represents an embodiment of the present invention.

FIG. 9B illustrates a unit cell of the photonic crystal shown in FIG. 9A that represents an embodiment of the present invention.

FIG. 15 shows three different transmission spectra, each transmission spectrum corresponds to a photonic crystal lattice constant a.

DETAILED DESCRIPTION

Figure 1:
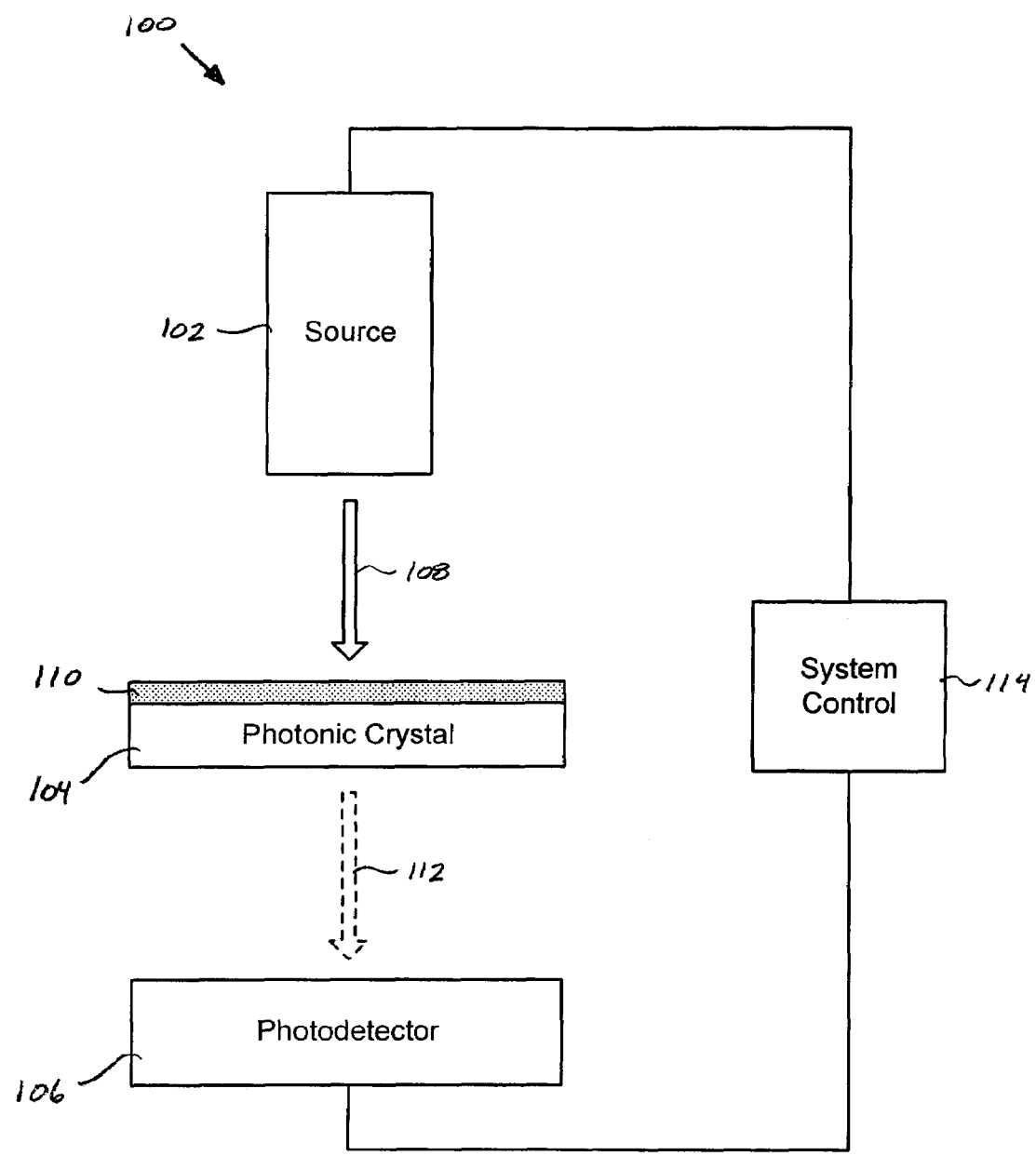
FIG. 1 illustrates a schematic representation of a first photonic-based sensor that represents an embodiment of the present invention.

Various embodiments of the present invention are directed to analyte detection methods and to photonic-based sensors that employ photonic crystal gratings to detect analytes. The analytes can be atoms, molecules, or any other chemical substance and can be in a gas, liquid, or solid phase. In the various photonic-based sensor embodiments described below, a number of structurally similar components have been provided with the same reference numerals and, in the interest of brevity, an explanation of their structure and function is not repeated.

EMBODIMENTS OF THE PRESENT INVENTION

FIG. 1 illustrates a schematic representation of a first photonic-based sensor 100 that represents an embodiment of the present invention. The photonic-based sensor 100 includes a source 102, a photonic crystal 104, and a photodetector 106. The source 102 can be a semiconductor laser, a p-n junction laser, or a heterojunction laser, such as a vertical cavity surface-emitting laser. The source 102 produces a focused beam of electromagnetic radiation, represented by directional arrow 108. The photonic crystal 104 can be composed of either a dielectric or semiconductor material and includes a substantially regular lattice of holes, which is called a "photonic crystal grating" or "photonic grating." The photonic crystal 104 and photonic crystal grating are described below with reference to FIGS. 6-9. An analyte 110 is situated on or in the photonic crystal grating of the photonic crystal 104. The photonic crystal 104 and the source 102 are positioned so that the beam of electromagnetic radiation 108 is directed substantially perpendicular to the photonic crystal grating. The electromagnetic radiation 108 irradiates the analyte 110 and the photonic crystal grating to produce a transmission spectrum represented by a dashed-line directional arrow 112. The transmission spectrum 112 is detected by the photodetector 106, which can be a p-i-n photodetector, an avalanche photodiode, or a depletion layer photodiode. The photonic-based sensor 100 also includes a system control 114, which can be used to collect and store the transmission spectrum output from the photodetector 106. Based on the transmission spectrum output from the photodetector 106, the system control 114, or a photonic-based sensor 100 operator, can adjust the orientation of the source 102 and the photonic crystal 104 so that the electromagnetic radiation is directed substantially perpendicular to the photonic crystal grating of the photonic crystal 104. The system control 114 may also tune the frequency range or wavelength range of the electromagnetic radiation 108 produced by the source 102.

Figure 2:
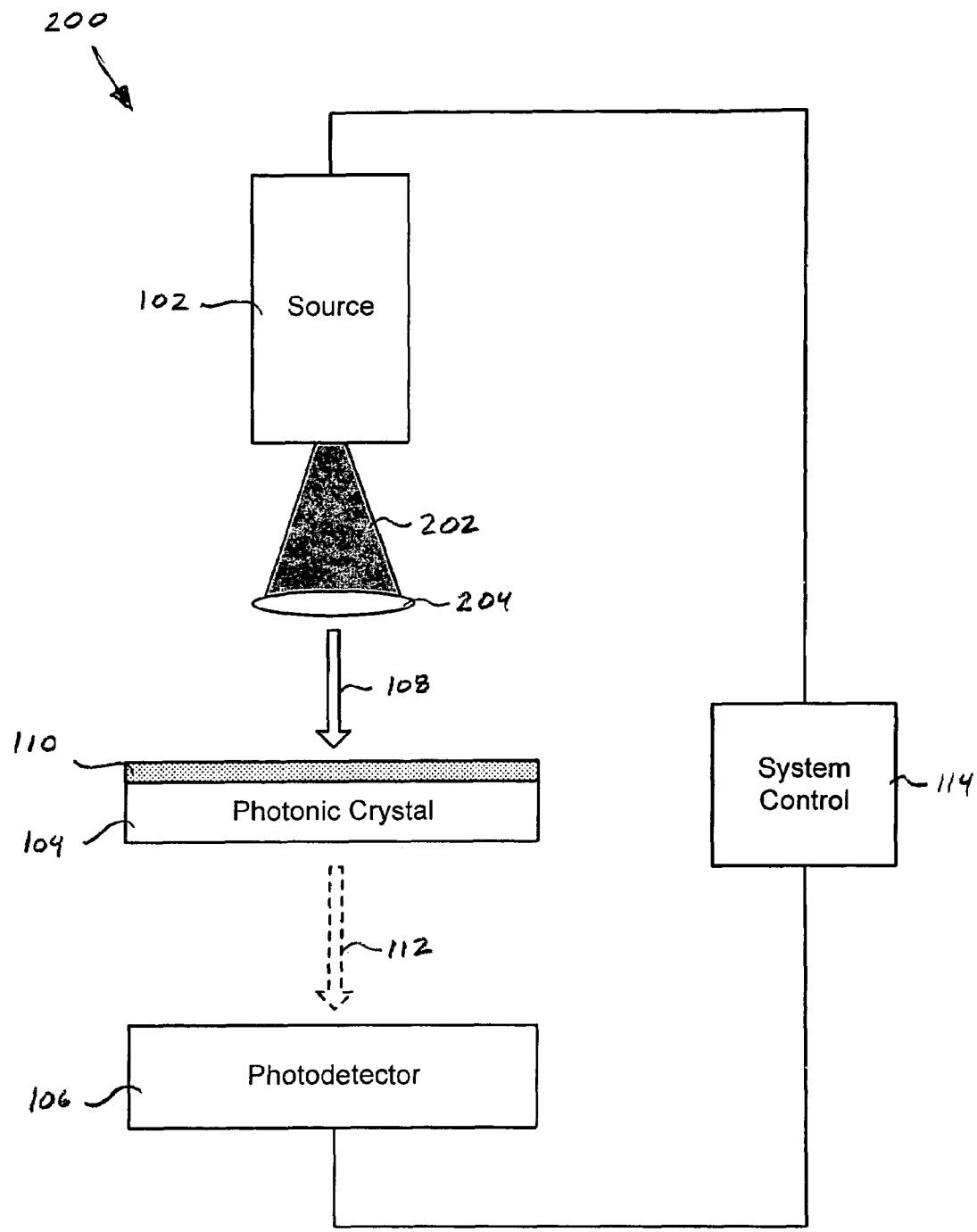
FIG. 2 illustrates a schematic representation of a second photonic-based sensor that represents an embodiment of the present invention.

FIG. 2 illustrates a schematic representation of a second photonic-based sensor 200 that represents an embodiment of the present invention. As shown in FIG. 2, the source 102 can be a light-emitting diode that emits an unfocused beam of electromagnetic radiation 202. The photonic-based sensor 200 includes a lens 204 that focuses the unfocused beam of electromagnetic radiation onto the analyte and the photonic crystal grating of the photonic crystal 104. Note that in alternate embodiments of the present invention, the photonic-based sensor 200 may include two or more lens to focus the beam of electromagnetic radiation produced by the source 102 onto the photonic crystal grating of the photonic crystal 104.

Figure 3:
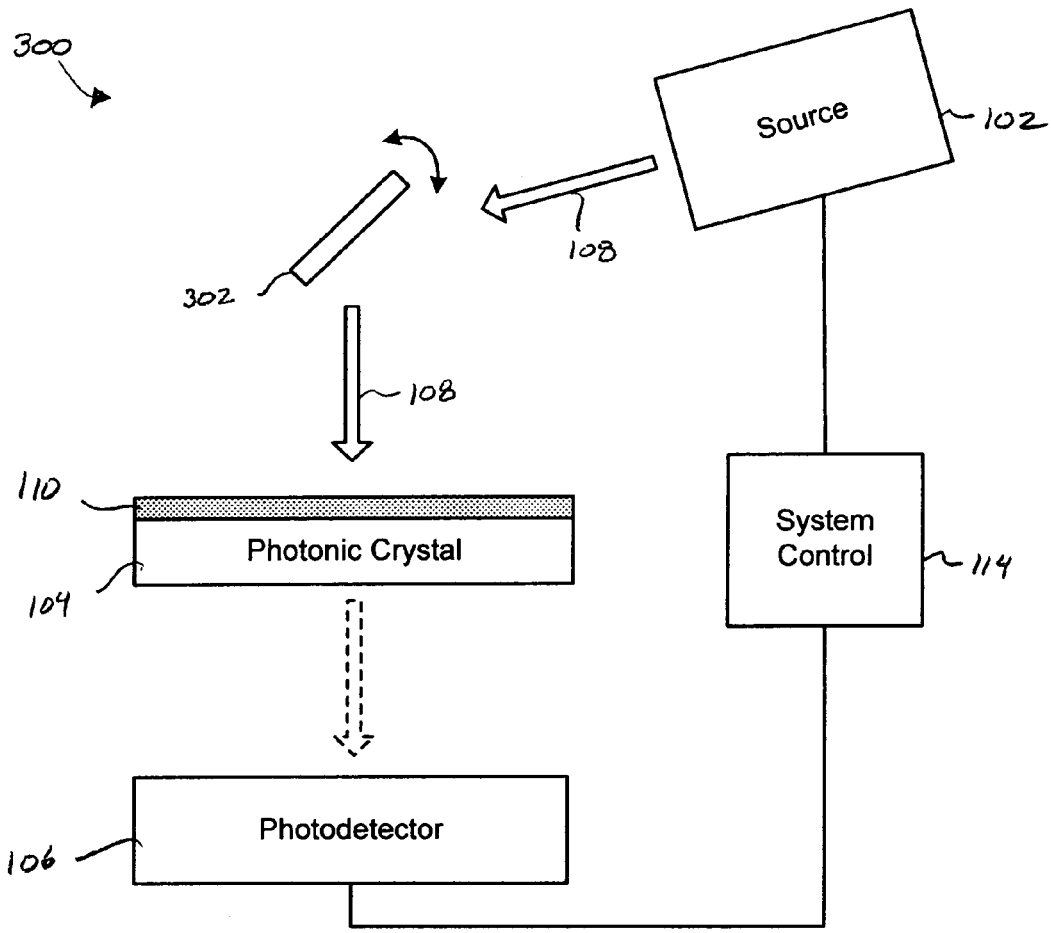
FIG. 3 illustrates a schematic representation of a third photonic-based sensor that represents an embodiment of the present invention.

FIG. 3 illustrates a schematic representation of a third photonic-based sensor 300 that represents an embodiment of the present invention. As shown in FIG. 3, the source 102 is positioned so that the electromagnetic radiation 108 output from the source 102 is not directed perpendicular to the plane of the photonic crystal 104. The photonic-based sensor 300 includes a mirror 302 that directs the electromagnetic radiation 108 output from the source 102 into a direction that is substantially perpendicular to the plane of the photonic crystal 104. The mirror 302 is included so that based on the data output from the photodetector 106, the system control 114, or a photonic-based sensor 300 operator, can adjust the position of the mirror 302 rather than the position of the source 102 to direct the electromagnetic radiation.

The transmission spectrum 112 output from the photonic crystal 104 is composed of a pattern of resonances. Each analyte has an associated pattern of resonances that can be used to detect and identify particular analytes. However, the transmission spectrum can vary according to the configuration, position, and material used to fabricate the photonic crystal 104. Using a transmission spectrum to detect and identify an analyte and how the transmission spectrum depends on the configuration and materials used to fabricate the photonic crystal is described below in the Examples subsection.

Figure 4:
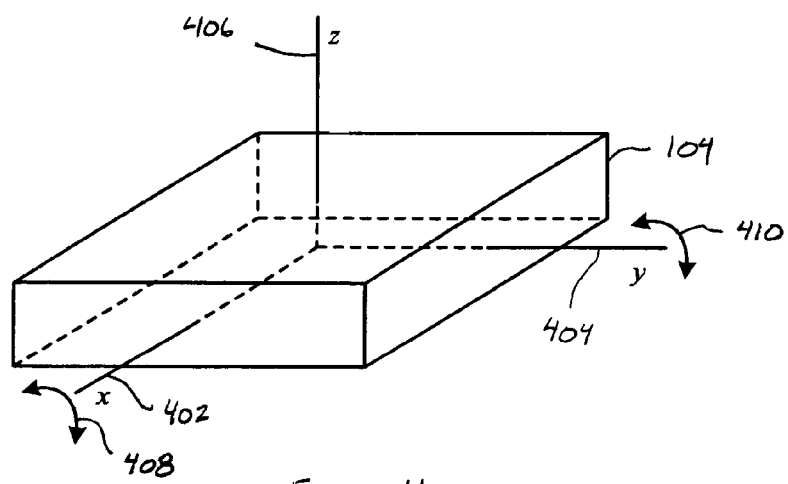
FIG. 4 illustrates an isometric view of positioning a photonic crystal within the photonic-based sensors shown in FIGS. 1-3 that represents an embodiment of the present invention.

In alternate embodiments of the present invention, the position of the photonic crystal 104 can also be adjusted so that the beam of electromagnetic radiation 108 is directed substantially perpendicular to the plane of the photonic crystal 104. FIG. 4 illustrates an isometric view of the photonic crystal 104 that represents an embodiment of the present invention. As shown in FIG. 4, the origin of a Cartesian coordinate system is located at the center of the photonic crystal 104. The x-coordinate axis 402 and the y-coordinate axis 404 lie in the plane of the photonic crystal 104, and the z-coordinate axis 406 is normal to the plane of the photonic crystal 104. The photonic crystal grating, described below with reference to FIGS. 6-9, lies in the xy-coordinate plane of the photonic crystal, and the electromagnetic radiation output from the source 102 is directed substantially parallel to the z-coordinate axis 406. In order to position the z-coordinate axis 406 so that the beam of electromagnetic radiation 108 is substantially parallel to the z-coordinate axis, the photonic crystal 104 can be placed on a stage (not shown) and independently rotated about the x-coordinate axis 402 and about the y-coordinate axis 404 as indicated by directional arrows 408 and 410, respectively. Systems, such as a stage, for positioning the photonic crystal 104 are well-known in the art and can be operated by the system control 114.

Figure 5B:
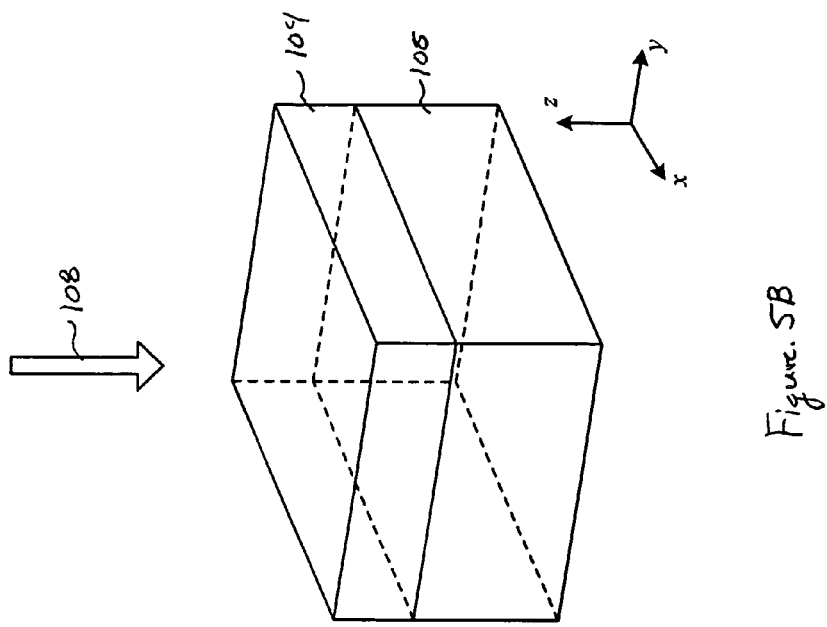
FIG. 5B shows a photonic crystal attached to a photodetector that represents an embodiment of the present invention.
Figure 5A:
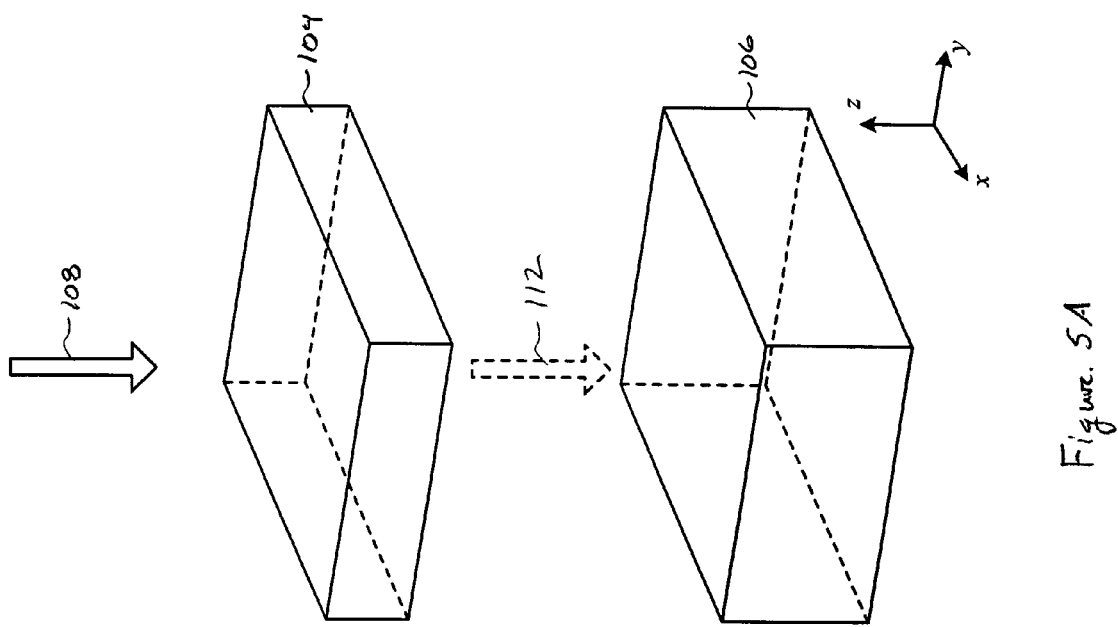
FIG. 5A shows a photonic crystal positioned separate from a photodetector that represents an embodiment of the present invention.

In alternate embodiments of the present invention, the photonic crystal 104 and the photodetector 106 can be positioned separate from one another or the photonic crystal 104 can be attached to the photodetector 106. FIG. 5A shows the photonic crystal 104 positioned separate from the photodetector 106 that represents an embodiment of the present invention. The beam of electromagnetic radiation 108 produced by the source 102 (not shown) is transmitted into the photonic crystal 104 substantially parallel to the z-coordinate axis. The electromagnetic radiation 108 irradiates the photonic crystal grating and the analyte to produce the transmission spectrum 112, which is transmitted to the photodetector 106. FIG. 5B shows the photonic crystal 104 attached to the photodetector 106 that represents an embodiment of the present invention. The electromagnetic radiation 108 produced by the source 102 (not shown) is also transmitted into the photonic crystal 104 substantially parallel to the z-coordinate axis. However, the electromagnetic radiation 108 irradiates the photonic crystal grating and the analyte to produce a transmission spectrum, which is detected directly by the photodetector 106.

In general, photonic crystals are photonic devices comprised of two or more materials with dielectric properties that, when combined together in a regular pattern, can modify the propagation characteristics of electromagnetic radiation. The books *Fundamentals of Optical Waveguides*, by Katsunari Okamoto, Elsevier Inc. 2005; *Optical Waveguide Theory*, by Snyder and Love, Chapman and Hall, London, 1983; and *Photonic Crystals*, by Jean-Michel Lourtioz, Springer-Verlag, Berlin, 2005 are just of few of many references that provide descriptions of photonic crystals. The photonic crystal 104 can be composed of a dielectric material or a semiconductor material. For example, the photonic crystal 104 can be composed of $SiO_2$, SiN, or a semiconductor, such as Si, or binary, ternary, or quaternary II-VI or III-V semiconductor compounds. For example, the photonic crystal 104 can be composed of either ZnTe or CdSe, both II-VI semiconductor compounds, or either GaAs or InP, both III-V semiconductor compounds. The type of material chosen for the photonic crystal 104 depends on the dimensions and configuration of the photonic crystal grating and on the frequency or wavelength range of electromagnetic radiation used.

Figure 6A:
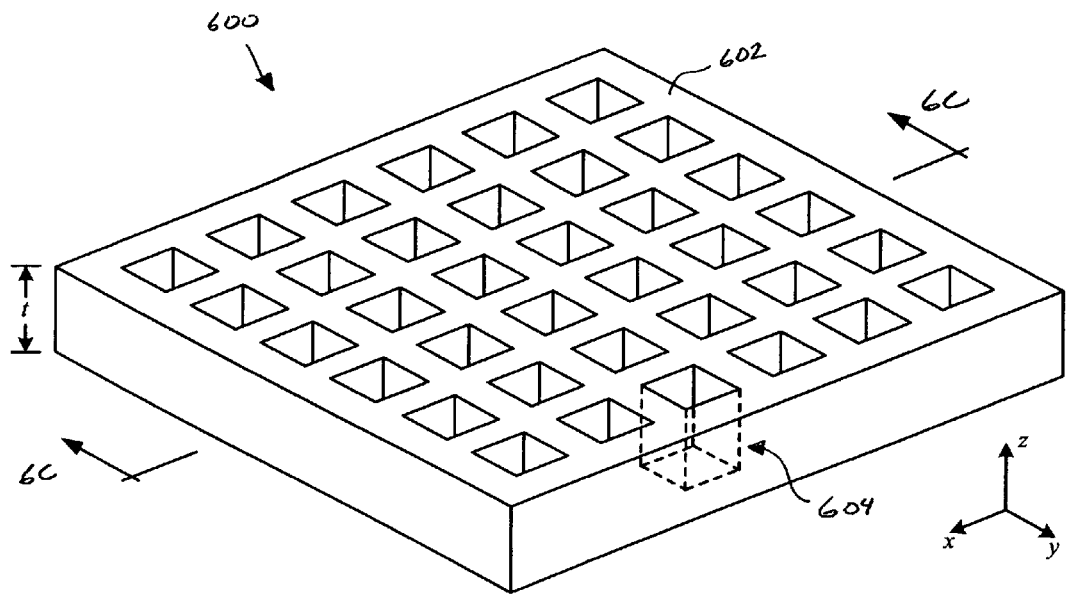
FIG. 6A illustrates an isometric view of a first two-dimensional photonic crystal that represents an embodiment of the present invention.
Figure 6B:
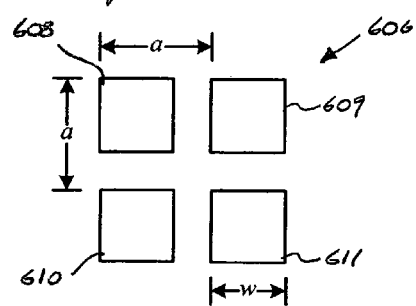
FIG. 6B illustrates a unit cell of the photonic crystal shown in FIG. 6A that represents an embodiment of the present invention.
Figure 6C:
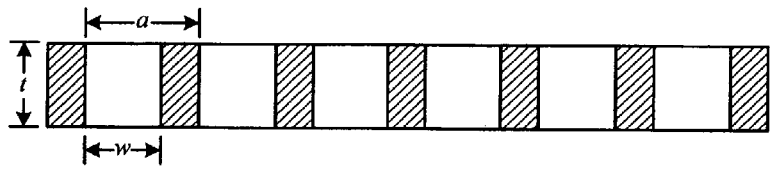
FIG. 6C illustrates a cross-sectional view of the photonic crystal shown in FIG. 6A that represents an embodiment of the present invention.

Certain embodiments of the present invention employ two-dimensional photonic crystals having a substantially regular lattice of holes fabricated in a dielectric or semiconductor slab. The lattice of holes can be fabricated using one of many well-known lithographic or etching techniques. FIG. 6A illustrates an isometric view of a two-dimensional photonic crystal 600 that represents an embodiment of the present invention. The photonic crystal 600 is composed of a slab 602 of dielectric or semiconductor material and a lattice of holes that lie in the xy-plane of the photonic crystal 600. Each hole in the lattice spans the thickness or height t of the photonic crystal 600. For example, a hole 604 spans the height of the slab 602. The holes can be air holes or composed of a dielectric or semiconductor material with a different dielectric constant from that of the material the slab 602. As shown in FIG. 6A, the holes are arranged in a substantially square lattice configuration. FIG. 6B illustrates a unit cell 606 of the photonic crystal 600 that represents an embodiment of the present invention. The unit cell 606 is composed of four substantially square shaped holes 608-611 of width w that are arranged in a substantially square configuration with a lattice constant a. FIG. 6C illustrates a cross-sectional view of the photonic crystal 600 that represents an embodiment of the present invention.

Figure 7A:
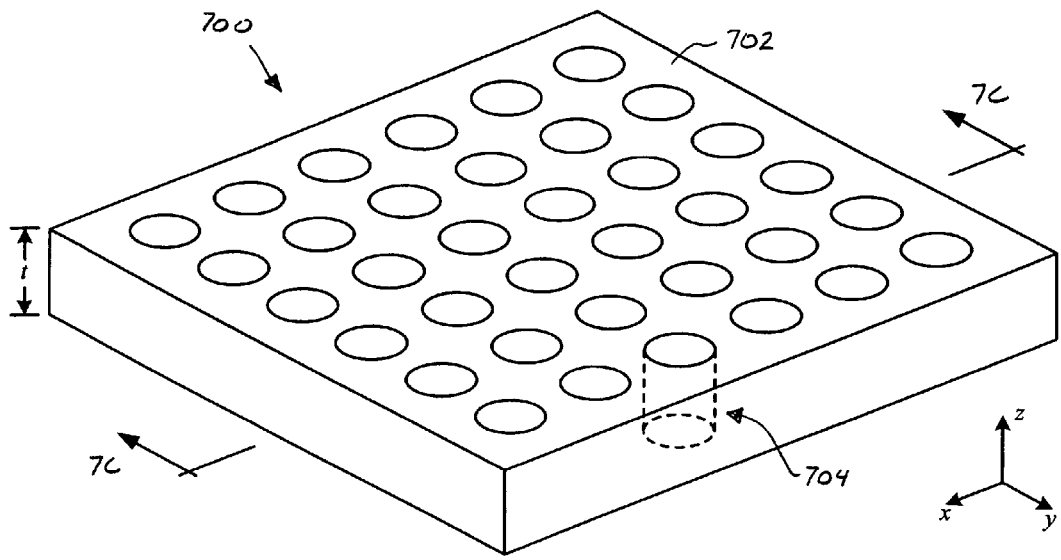
FIG. 7A illustrates an isometric view of a second two-dimensional photonic crystal that represents an embodiment of the present invention.
Figure 7B:
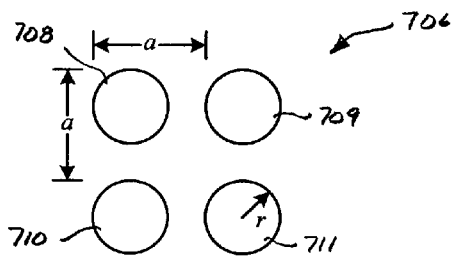
FIG. 7B illustrates a unit cell of the photonic crystal shown in FIG. 7A that represents an embodiment of the present invention.
Figure 7C:
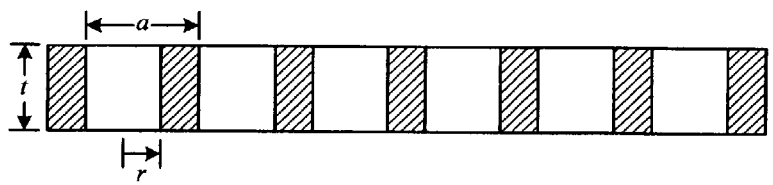
FIG. 7C illustrates a cross-sectional view of the photonic crystal shown in FIG. 7A that represents an embodiment of the present invention.

In an alternate embodiment of the present invention, the lattice holes can have different shapes. FIG. 7A illustrates an isometric view of a second kind of two-dimensional photonic crystal 700 that represents an embodiment of the present invention. The photonic crystal 700 is composed of a slab 702 of dielectric or semiconductor material and a lattice of holes that lie in the xy-plane of the photonic crystal 700. Each hole in the lattice spans the thickness or height t of the photonic crystal 700, such as hole 704. The holes can be air holes or composed of a dielectric or semiconductor material with a different dielectric constant from that of the material the slab 702. As shown in FIG. 7A, the holes are arranged in a substantially square lattice configuration. FIG. 7B illustrates a unit cell 706 of the photonic crystal 700 that represents an embodiment of the present invention. The unit cell 706 is composed of four substantially round holes 708-711 with radii r that are arranged in a substantially square configuration with a lattice constant a. FIG. 7C illustrates a cross-sectional view of the photonic crystal 700 that represents an embodiment of the present invention.

In alternate embodiments of the present invention, the lattice of holes can have different unit cell configurations. FIG. 8A illustrates an isometric view of a third kind of two-dimensional photonic crystal 800 that represents an embodiment of the present invention. The photonic crystal 800 is composed of a slab 802 of dielectric or semiconductor material and a lattice of substantially square holes arranged in a substantially triangle lattice configuration that lie in the xy-plane of the photonic crystal 800. FIG. 8B illustrates a unit cell 804 of the photonic crystal 800 that represents an embodiment of the present invention. The unit cell 804 is composed of three substantially square holes 806-808 arranged in a substantially triangular configuration.

FIG. 9A illustrates an isometric view of a fourth kind of two-dimensional photonic crystal 900 that represents an embodiment of the present invention. The photonic crystal 900 is composed of a slab 902 of dielectric or semiconductor material and a lattice of substantially round holes arranged in a substantially triangle lattice configuration that lie in the xy-plane of the photonic crystal 900. FIG. 9B illustrates a unit cell 904 of the photonic crystal 900 that represents an embodiment of the present invention. The unit cell 904 is composed of three substantially round holes 906-908 arranged in a substantially triangular configuration.

Two-dimensional photonic crystals are typically used to filter out bands of electromagnetic radiation when the beam of electromagnetic radiation is directed into the photonic crystal in the xy-plane. These filtered out bands of electromagnetic radiation are typically referred to as "photonic bandgaps." However, in the photonic-based sensors described above with reference to FIGS. 1-5, an analyte is placed on either the top surface of the photonic crystal or within the lattice of holes, and a beam of electromagnetic radiation output from a source is directed substantially parallel to the z-coordinate axis. In other words, the lattice of holes serves as a grating that supports the analyte and may also be called a "photonic crystal grating" or a "photonic grating." As a result, certain frequency bands, or wavelength bands, of electromagnetic radiation couple with and resonate in the photonic crystal grating. Electromagnetic radiation corresponding to these wavelength bands are reflected back. In other words, a portion or all of the electromagnetic radiation having wavelengths within these bands resonate with the photonic crystal and the analyte and are not transmitted through the photonic crystal. These wavelength bands are referred to as "resonances." For example, the photonic crystal 600 can be used in the photonic-based sensors described above with reference to FIGS. 1-3. The analyte is situated on or in the photonic crystal grating, and the electromagnetic radiation 108 output from the source 102, shown in FIGS. 1-3, is directed to the photonic crystal 600 in a direction that is substantially parallel to the z-coordinate axis. The electromagnetic radiation 108 irradiates the photonic crystal grating. Electromagnetic radiation having wavelengths that do not couple with the analyte and the photonic crystal grating are transmitted through the photonic crystal. However, other wavelengths of the electromagnetic radiation that couple with the analyte and the photonic crystal grating are reflected back. The wavelengths that couple with the analyte and the photonic crystal grating can be identified as troughs or regions of low transmittance in a transmission spectrum and can be used to identify the analyte, as described below with reference to the Examples.

Figure 10:
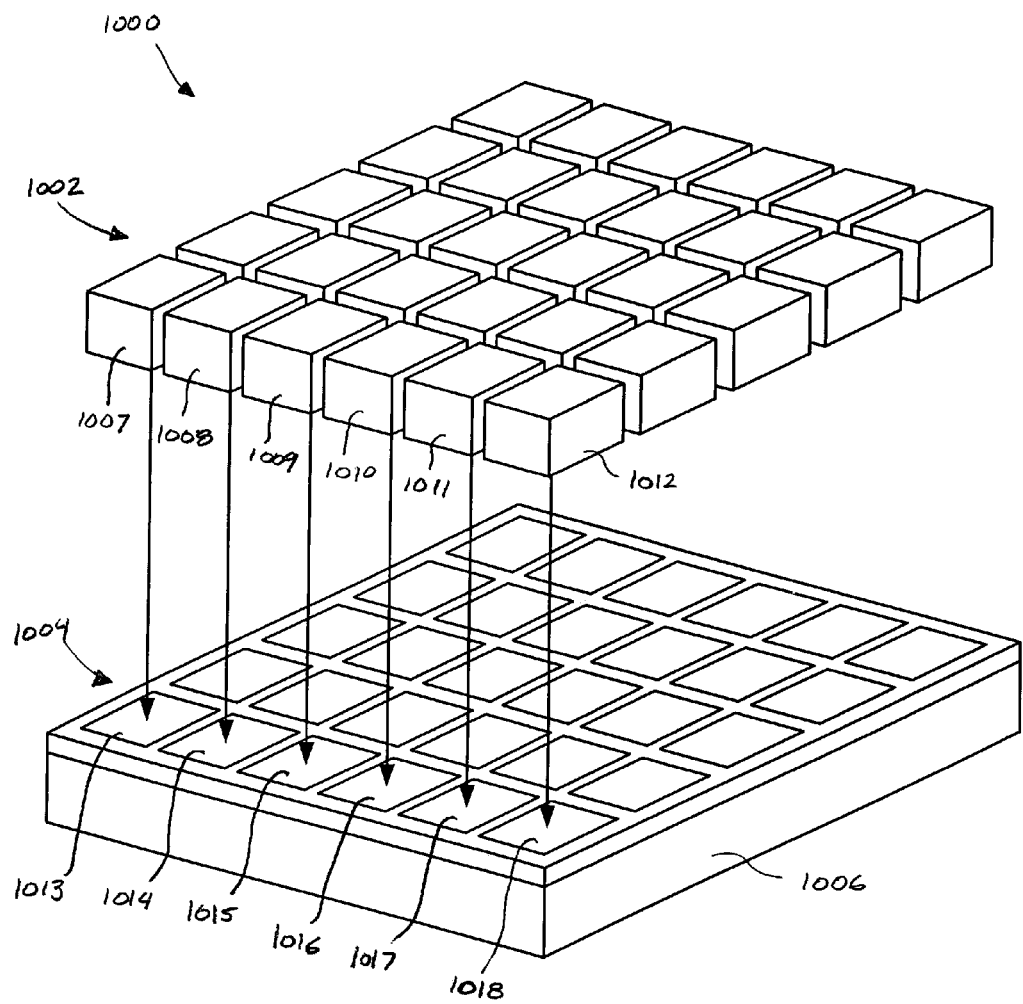
FIG. 10 illustrates an isometric view of a photonic-based sensor configured to detect a number of different analytes that represents an embodiment of the present invention.

In alternate embodiments of the present invention, a number of photonic-based sensors described above with reference to FIGS. 1-3 can be integrated to form a photonic-based sensor capable of detecting a number of different analytes in parallel. FIG. 10 illustrates an isometric view of a photonic-based sensor 1000 configured to detect a number of different analytes that represents an embodiment of the present invention. As shown in FIG. 10, the photonic-based sensor 1000 is composed of an array of 30 separate sources 1002, an array of 30 corresponding photonic crystals 1004, and a detector 1006. For example, sources 1007-1012 correspond to the photonic crystals 1013-1018, respectively. Each source can output a different wavelength range of electromagnetic radiation, and each corresponding photonic crystal can be configured with a different photonic crystal grading in order to detect one of 30 different analytes. For example, the sources 1007 and the corresponding photonic crystal 1013 can be configured to detect one of 30 different analytes situated on the array of photonic crystals 1004. The detector 1006 can be composed of 30 separate photodetectors, each photodetector located beneath a photonic crystal in the array of photonic crystals 1004.

EXAMPLES

The performance of a photonic-based sensor fabricated in accordance with the embodiments of the present invention depends on a number of factors including the range of wavelengths over which electromagnetic radiation, the dielectric constant of the photonic crystal, the kind, size, lattice spacing, and arrangement of the holes comprising the photonic crystal grating, the thickness of the photonic crystal, and the angle of electromagnetic radiation incident upon the photonic crystal. The performance can be assessed by determining a normalized sensitivity and a quality factor of the photonic-based sensor. The normalized sensitivity is given by:

$$\frac{\Delta\lambda}{\lambda_0 \Delta n}$$

where $\lambda_0$ is the wavelength of electromagnetic radiation output from the source 102;

$\Delta\lambda$ is the change in the wavelength of the electromagnetic radiation as a result of irradiating the analyte and grating; and $\Delta n$ is the difference between the refractive index of the grating and the refractive index of the analyte.

The sensitivity ranges from "0" to "1." A sensitivity value close "0" indicates low sensitivity, and a sensitivity value close to "1" indicates high sensitivity. The higher the sensitivity, the more reliable the results obtained from the photonic-based sensor. In general, the quality factor is given by:

$$Q = \frac{f_0}{\Delta f}$$

where $f_0$ is the resonant frequency of the grating; and $\Delta f$ is the width of the range of frequencies for which the energy is about ½ the energy peak value. The quality factor compares the frequency at which electromagnetic radiation resonates to the rate at which energy stored in the electromagnetic radiation dissipates. A high quality factor indicates a low rate of energy dissipation relative to the resonance frequency, and a low quality factor indicates a high rate of energy dissipation relative the resonance frequency. The higher the quality factor, the better and easier it may be to identify an analyte as described below.

FIGS. 11-16 show plots of transmission spectra for various photonic crystal gratings that represent embodiments of the present invention. The transmission spectra are obtained using the rigorous coupling wave analysis described in M. G. Moharam et al., "Diffraction analysis of dielectric surface relief gratings," *J. Opt. Soc. Am.* 72, 1385-1392 (1982) and in L. Li, "New formation of the Fourier modal method for crossed surface relief gratings," *J. Opt. Soc. Am. A* 14, 2758-2767 (1997). The photonic crystals are assumed to be free standing, of infinite xy-planar dimensions, and have a regular square lattice of square holes, as shown in FIG. 6. The plots shown in FIGS. 11-13, 15 and 16 show how the transmission spectra vary according to the thickness of the photonic crystal, the incident angle of electromagnetic radiation upon the photonic crystal, the size of holes in the photonic crystal grating, and the dielectric constant of the photonic crystal. In FIGS. 11-13, 15 and 16, the vertical axes represent the fraction of electromagnetic radiation transmitted through the photonic crystal and analyte in the z-coordinate axis direction. In FIGS. 11-13, and 16, the horizontal axes correspond to a range of electromagnetic radiation wavelengths.

Figure 11:
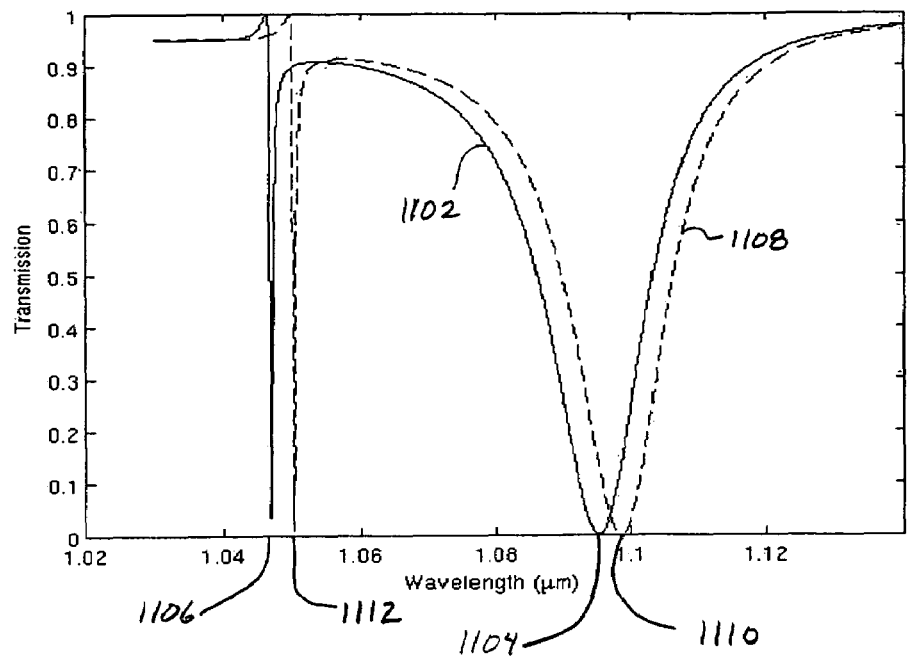
FIG. 11 shows a plot of two transmission spectra, each spectrum is associated with one of two different analytes situated on a first photonic crystal that represents an embodiment of the present invention.

FIG. 11 shows a plot of two transmission spectra for a $SiO_2$ photonic crystal grating with a equal to 1000 nm, t equal to 500 nm, and w equal to 800 nm. A first transmission spectrum 1102 corresponds to a first analyte with a dielectric constant of 1.0 filling the holes and region surrounding the photonic crystal. The first transmission spectrum 1102 has a first minimum 1104 at 1094.4 nm and a second minimum 1106 at 1047 nm. A second transmission spectrum 1108 corresponds to a second analyte with a dielectric constant of 1.01 filling the holes and region surrounding the photonic crystal. The second transmission spectrum 1108 has a first minimum 1110 at 1098.6 nm and a second minimum 1112 at 1050.3 nm. The sensitivity calculated for the first curve 1102 is 0.5843, and the sensitivity calculated for the second curve 1108 is 0.6304. The quality factor Q associated with the first minima 1104 and 1110 is 64, and the quality factor Q associated with the second minima 1106 and 1112 is 2618.

The shape of a transmission spectrum and location of the transmission-spectrum minima can be used to identify an analyte. For example, although the first transmission spectrum 1102 and the second transmission spectrum 1108 exhibit substantially similar shapes, the first and second analyte can be distinguished because the location of the minima 1110 and 1112 associated with the second analyte are shifted to larger wavelengths than the minima 1104 and 1106 associated with the first analyte. The minima 1104, 1106, 1110, and 1112 correspond to resonances. In other words, electromagnetic radiation having wavelengths within the resonances are prevented from being transmitted through the photonic crystal. Note that the higher the quality factor Q associated with a minimum the narrower or sharper the resonance. For example, the narrow resonances are associated with the second minima 1106 and 1112, each with a quality factor Q equal to 2618, while the broad resonances are associated with the first minima 1104 and 1110, each with a quality factor Q equal to 64. The narrower the resonances, the easier it is to identify an analyte. For example, the resonances centered about the first minima 1104 and 1110 overlap for transmissions that are greater than about 0.05. As a result, it may difficult to distinguish the first and second analytes. By contrast, the narrow resonances centered about the second minima 1106 and 1112 do not overlap. As a result, the first analyte associated with the second minimum 1106 can be more easily distinguished from the second analyte associated with the second minimum 1112.

Figure 12:
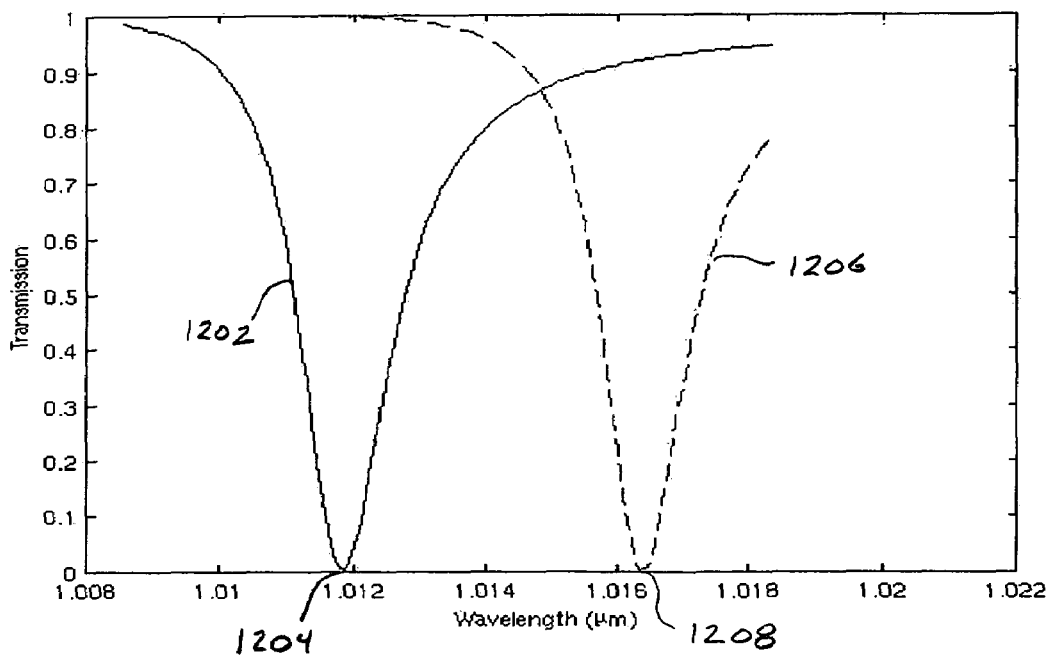
FIG. 12 shows a plot of two transmission spectra, each spectrum is associated with one of two different analytes situated on a second photonic crystal that represents an embodiment of the present invention.

As pointed out above, higher quality factors Q are more desirable because it is easier to distinguish the resonances associated with the analytes. As a result, in alternate embodiments of the present invention, the photonic crystal dimensions and grating configuration can be modified to try and maximize quality factors Q. FIG. 12 shows resonances associated with the photonic crystal used to produce the two transmission spectra in FIG. 11 except the thickness t of the photonic crystal is reduced from 500 nm to 100 nm. A first transmission spectrum 1202 corresponds to the first analyte with a dielectric constant of 1.0, and a second transmission spectrum 1206 corresponds to a second analyte with a dielectric constant of 1.01. The first transmission spectrum 1202 has a minimum 1204 at 1011.8 nm, and the second transmission spectrum 1206 has a minimum 1208 at 1016.4 nm. The minima 1204 and 1208 correspond to the first minima 1104 and 1110, shown in FIG. 11. However, because the thickness t has been reduced to 100 nm, the quality factor Q associated with the minima 1204 and 1208 is 632, and the sensitivity is increased to 0.9172. Note that unlike the resonances centered about the first minima 1104 and 1110, shown in FIG. 11, the resonances centered about the minima 1204 and 1208 do not overlap for transmission less than about 0.85. The transmission spectra 1202 and 1206 indicate that by reducing the thickness t of the photonic crystal, the quality factor Q increases, which corresponds to narrower resonances and makes identifying analytes according to resonance locations easier.

Although, the transmission spectra shown in FIG. 12 may seem counterintuitive, these results may be explained by considering the shape of a guided mode. Consider first the thin photonic crystal grating (t=100 nm). If one decomposes this mode into plane waves, the most dominant plane wave components have wavevectors that lie in the plane of the photonic crystal grating, which makes coupling to the plane waves of incident electromagnetic radiation weak. As a result, the quality factor Q increases. Now consider the photonic crystal with a relatively thicker photonic crystal grating (t=500 nm). Most of the electromagnetic radiation is concentrated within the photonic crystal grating, which makes the guided mode narrower in space. For this mode, the contribution of the electromagnetic waves with wavevectors directed away from the plane of the photonic crystal grating are higher than in the thin photonic crystal grating. As a result, coupling the photonic crystal grating with the incident electromagnetic radiation is stronger and the quality factor Q is smaller. In addition, the sensitivity of the thin photonic crystal grating is higher, because the guided mode in the photonic crystal grating is directed away from the plane of the photonic crystal grating, and the guided mode is more sensitive to changes in the dielectric constant of a surrounding analyte.

The transmission spectra described above are generated by assuming that the incident beam of the electromagnetic radiation is directed normal to the photonic crystal grating. However, in practice, a beam of electromagnetic radiation may be directed a few degrees away from normal. For example, when the angle of incidence with the photonic crystal and first analyte described above with reference to FIG. 11 are 0°, 1°, and 2°, the first resonance minima appear at 1095.4, 1095.3, and 1094.8 nm, respectively. By contrast, when the incident angles are 0° and 1°, the second photonic bang gap minima appear at 1047 nm and 1040.5 nm, respectively. The variations in the wavelengths of the relatively lower resonance minima are larger than variations in the refractive index of the analyte. Also, additional narrow resonances appear as the angle with the normal vector increases.

Figure 13:
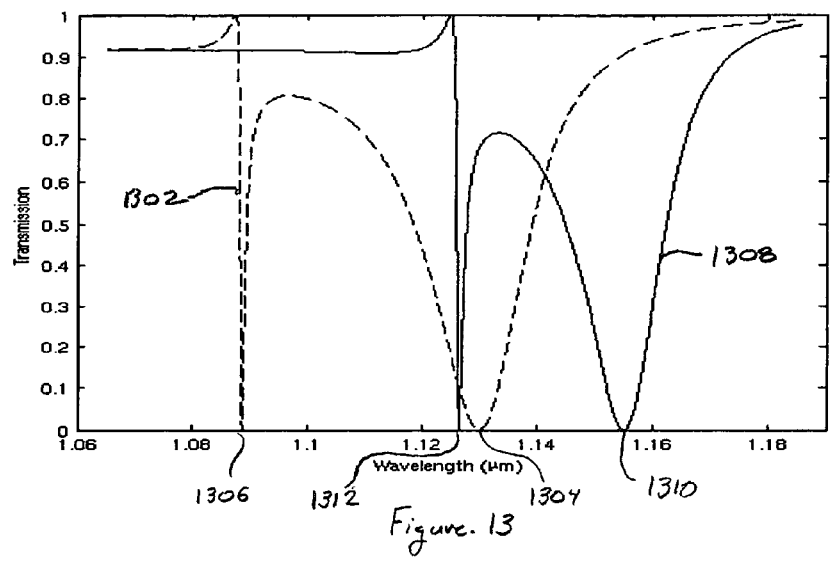
FIG. 13 shows a plot of two transmission spectra, each spectrum is associated one of two different analytes situated on a third photonic crystal that represents an embodiment of the present invention.

Reducing the size of the holes shifts the transmission spectrum to higher wavelengths. FIG. 13 shows two transmission spectra. The photonic crystal used to produce the transmission spectra is identical to the photonic crystal used to produce the transmission spectra shown in FIG. 11 except the width w of the holes are different. Transmission spectrum 1302 corresponds to holes with width 700 nm and has a first minimum 1304 at 1129.9 nm with a quality factor of 55 and a second minimum 1306 at 1088.6 nm with a quality factor Q of 990. Transmission spectrum 1308 corresponds to holes with width 600 nm and has a first minimum 1310 at 1155 nm with a quality factor Q of 68 and a second minimum 1312 at 1126.4 nm with a quality factor Q of 651.

Figure 14:
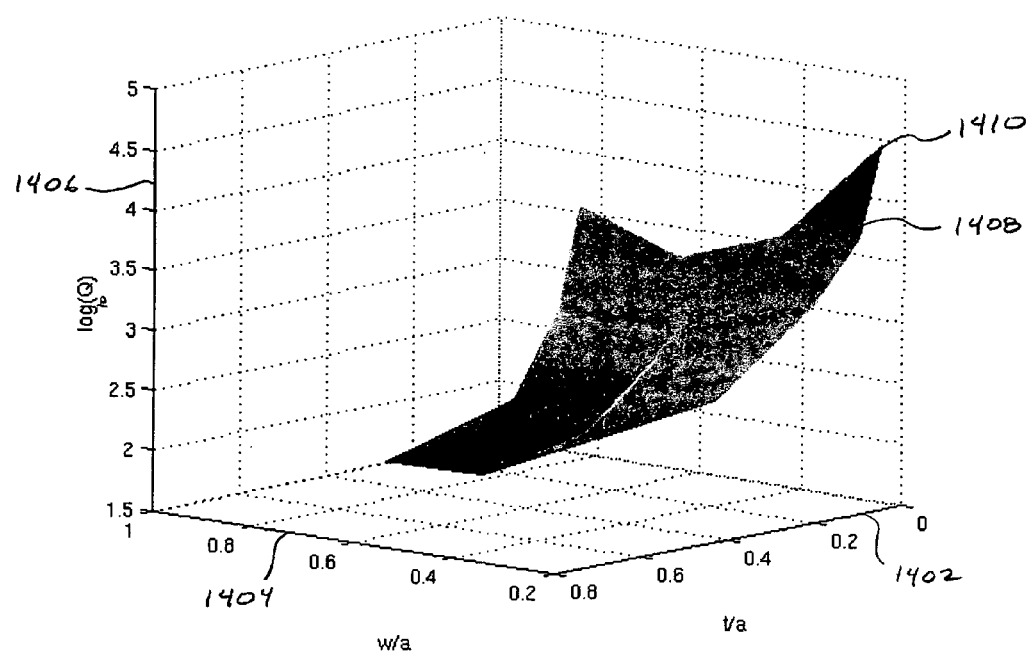
FIG. 14 shows how a quality factor Q varies as photonic crystal grating constants are varied.

As described above with reference to FIG. 12, larger quality factors Q are preferred. FIG. 14 shows how the quality factor Q varies as a function of w/a and t/a for a photonic crystal surrounded by an analyte with a dielectric constant of 1.0. The lattice constant a is 1000 nm. In FIG. 14, the axis 1402 corresponds to values for t/a, the axis 1404 corresponds to values for w/a, and vertical axis 1406 corresponds to $\log_{10}$ (Q). Surface 1408 represents $\log_{10}$ (Q) as a function of t/a and w/a, and shows that the quality factor increases as t/a and w/a decrease. In particular, a maximum quality factor Q 1410 of 33000 is achieved for w/a is equal to 0.2 and t/a is equal to 0.05.

Figure 15:
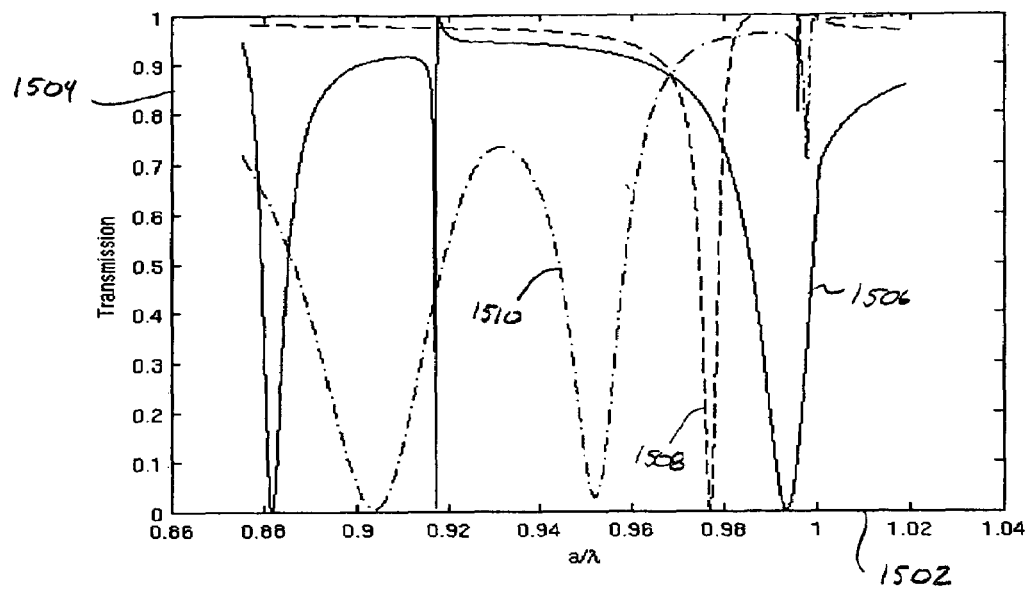

$SiO_2$ is nearly lossless for thicknesses around 1 μm. In fact, the imaginary part of the refractive index for $SiO_2$, which corresponds to absorption, is approximately zero. However, the absorption electromagnetic radiation increases as the thickness of $SiO_2$ increases. FIG. 15 shows three different transmission spectra, each transmission spectrum corresponds to the photonic crystal described above with reference to FIG. 11 except the lattice constant a is varied. In FIG. 15, horizontal axis 1502 corresponds to a dimensionless quantity a/λ and vertical axis 1504 corresponds to the transmission. Transmission spectrum 1506 corresponds to a photonic crystal with a lattice constant a equal to 600 nm, transmission spectrum 1508 corresponds to a photonic crystal with a lattice constant a equal to 3000 nm, and transmission spectrum 1510 corresponds to a photonic crystal with a lattice constant of a equal to 9000 nm. The ratios t/a and w/a are the same for the three different photonic crystals used to generate the transmission spectra 1506, 1508, and 1510. For the photonic crystal with a equal to 600 nm, the transmission spectrum 1506 is similar to the transmission spectra 1102 and 1104, shown in FIG. 11. For the photonic crystal with a equal to 3000 nm, the refractive index of $SiO_2$ is smaller relative to incident electromagnetic radiation with a wavelength λ equal to 1000 nm. As a result, the resonances for the corresponding photonic crystal are narrower, because the guided modes are extended and coupling with plane waves of the incident electromagnetic radiation is weaker. For the photonic crystal with a equal to 9000 nm, the $SiO_2$ has strong absorption band at around 7800 nm which correspond to wide resonances.

Figure 16:
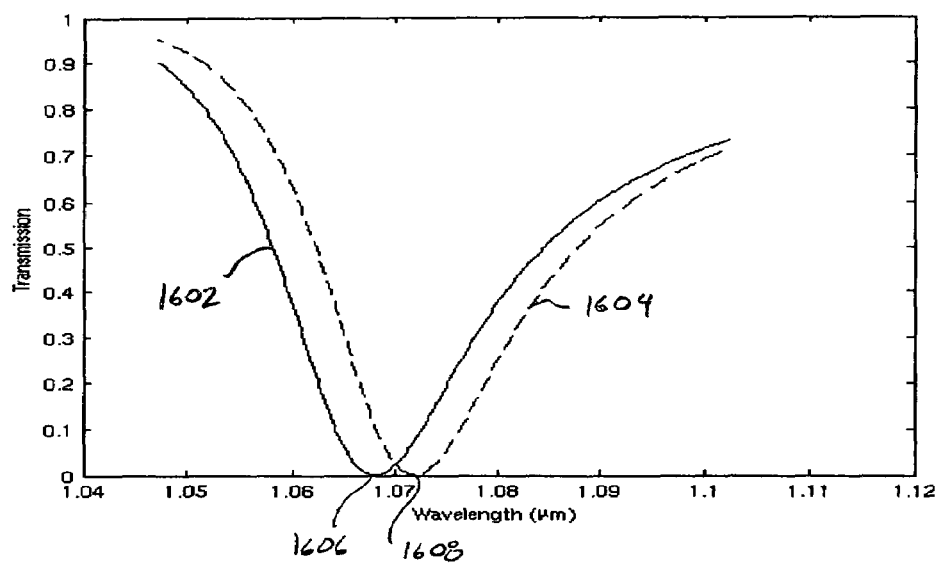
FIG. 16 shows a plot of two transmission spectra, each spectrum is associated with one of two different analytes situated on a SiN photonic crystal that represents an embodiment of the present invention.

FIG. 16 shows transmission spectra for a SiN photonic crystal with photonic crystal grating parameters a, t, and w identical to the $SiO_2$ photonic crystal described above with reference to FIG. 12. A first transmission spectrum 1602 corresponds to the first analyte with a dielectric constant of 1.0, and a second transmission spectrum 1604 corresponds to a second analyte with a dielectric constant of 1.01. However, unlike the transmission spectra 1202 and 1206 for the corresponding analytes, shown in FIG. 12, the corresponding minima 1606 and 1608 the resonances overlap for transmissions larger than about 0.5. In addition, the quality factor Q associated with minima 1606 and 1608 is 40 and the sensitivity is 0.7116, which correspond to a drop of about 15 in the quality factor Q and a drop of about a 20% in the sensitivity. These changes are due to the larger refractive index for SiN, which confines the guided modes to the photonic crystal grating.

Although the present invention has been described in terms of particular embodiments, it is not intended that the invention be limited to these embodiments. Modifications within the spirit of the invention will be apparent to those skilled in the art. In an alternate embodiment of the present invention, those skilled in the art would recognize that three-dimensional photonic crystals can be used in place of two-dimensional photonic crystals. The lattice configuration is not limited to square and triangular lattice configurations. For example, in alternate embodiments of the present invention, the lattice configurations can have other configuration well-known in the art, such as an Archimedean tiling. The photonic crystals can also be two and three-dimensional photonic crystals of the woodpile type, which is composed of periodic arrays of dielectric or semiconductor rods. In alternate embodiments of the present invention, a single source can be used to irradiate the photonic crystals shown in FIG. 10 rather separate sources.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purposes of illustration and description. They are not intended to be exhaustive of or to limit the invention to the precise forms disclosed. Obviously, many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents:

What is claimed is:

1. A photonic-based sensor comprising:
    a source configured to output electromagnetic radiation;
    a photonic crystal having a photonic crystal grating positioned to receive the electromagnetic radiation, wherein the electromagnetic radiation interacts with the photonic crystal grating and an analyte situated on or in the photonic crystal grating to produce a transmission spectrum that characterizes the analyte; and
    a photodetector positioned to detect the transmission spectrum.

2. The photonic-based sensor of claim 1 further comprising a system control configured to receive and store the transmission spectrum and based on the transmission spectrum adjust the frequency range of the electromagnetic radiation and the angle between the source and the photonic crystal grating.

3. The photonic-based sensor of claim 1 wherein the source further comprises one of:
    a light-emitting diode;
    a semiconductor laser;
    a p-n junction laser; and
    a heterojunction laser.

4. The photonic-based sensor of claim 1 wherein the photonic crystal grating positioned to receive the electromagnetic radiation further comprises orienting the photonic crystal so that the electromagnetic radiation is directed substantially perpendicular to the photonic crystal grating.

5. The photonic-based sensor of claim 1 wherein the photodetector further comprises one of:
    a p-i-n photodetector;
    an avalanche photodiode; and
    a depletion layer photodiode.

6. The photonic-based sensor of claim 1 further comprises a mirror to direct the electromagnetic radiation to the photonic crystal grating.

7. The photonic-based sensor of claim 1 further comprises one or more lens that focuses the electromagnetic radiation onto the photonic crystal grating.

8. The photonic-based sensor of claim 1 wherein the analyte further comprises one of:
    a gas;
    a liquid; and
    a solid.

9. An integrated photonic-based sensor comprising a plurality of photonic-based sensors each of which is configured in accordance with claim 1.

10. An analyte detection method comprising:
    situating the analyte on or in a photonic crystal grating;
    irradiating the analyte and the photonic crystal grating with electromagnetic radiation to produce a transmission spectrum that characterizes the analyte; and
    detecting the electromagnetic radiation spectrum.

11. The method of claim 10 wherein the photonic crystal grating further comprises positioning a photonic crystal so that the photonic crystal grating receives the analyte.

12. The method of claim 10 wherein irradiating further comprises generating the electromagnetic radiation using one of:
    a light-emitting diode;
    a semiconductor laser;

a p-n junction laser; and a heterojunction laser.

13. The method of claim 10 wherein irradiating the analyte and the photonic crystal grating further comprises focusing the electromagnetic radiation onto the photonic crystal grating using one or more lenses.

14. The method of claim 10 wherein irradiating the analyte and the photonic crystal grating further comprises adjusting a frequency range of the electromagnetic radiation to irradiate the analyte and the photonic crystal grating.

15. The method of claim 10 wherein detecting the spectrum of the electromagnetic radiation further comprises using one of:

a p-i-n photodetector;

an avalanche photodiode; and a depletion layer photodiode.

16. An integrated photonic-based sensor for detecting a plurality of different analytes, the integrated photonic-based sensor comprising:

a plurality of sources, each source configured to output electromagnetic radiation;

a plurality of photonic crystals, each photonic crystal corresponding to one of the sources and having a photonic crystal grating and an analyte situated on or in the photonic crystal grating such that the electromagnetic radiation output from a corresponding source interacts with the photonic crystal grating and the analyte to produce a corresponding transmission spectrum that characterizes the analyte; and a plurality of photodetectors, each photodetector corresponding to one of the photonic crystals and positioned to detect the transmission spectrum output from the corresponding photonic crystals.

17. The integrated photonic-based sensor of claim 16 further comprising a system control configured to receive and store the transmission spectra and based on the transmission spectra adjust the frequency range of the electromagnetic radiation and the angle between the each source and the corresponding photonic crystal grating.

18. The integrated photonic-based sensor of claim 16 wherein each source further comprises one of:

a light-emitting diode;

a semiconductor laser;

a p-n junction laser; and a heterojunction laser.

19. The integrated photonic-based sensor of claim 16 wherein each of the photonic crystal gratings are positioned to receive the electromagnetic radiation substantially perpendicular to the photonic crystal grating.

20. The integrated photonic-based sensor of claim 16 wherein each photodetector further comprises one of:

a p-i-n photodetector;

an avalanche photodiode; and a depletion layer photodiode.

* * * * *